United States Patent
Su et al.

(10) Patent No.: US 9,375,424 B2
(45) Date of Patent: Jun. 28, 2016

(54) COMPOUNDS THAT TREAT MALARIA AND PREVENT MALARIA TRANSMISSION

(75) Inventors: Xin-zhuan Su, Potomac, MD (US); Jing Yuan, Rockville, MD (US); Dipak Raj, Providence, RI (US); Sittiporn Pattaradilokrat, Rockville, MD (US); Ron Johnson, Derwood, MD (US); Ruili Huang, Rockville, MD (US)

(73) Assignee: The United States of America, as represented by the Secretary, Dept. of Health and Human Services, Washington, DC (US)

( * ) Notice: Subject to any disclaimer, the term of this patent is extended or adjusted under 35 U.S.C. 154(b) by 530 days.

(21) Appl. No.: 13/392,668

(22) PCT Filed: Aug. 27, 2010

(86) PCT No.: PCT/US2010/047019
§ 371 (c)(1),
(2), (4) Date: Apr. 19, 2012

(87) PCT Pub. No.: WO2011/025969
PCT Pub. Date: Mar. 3, 2011

(65) Prior Publication Data
US 2012/0196882 A1    Aug. 2, 2012

Related U.S. Application Data

(60) Provisional application No. 61/237,417, filed on Aug. 27, 2009.

(51) Int. Cl.
*A61K 31/4535* (2006.01)
*A61K 8/49* (2006.01)
*A61K 45/06* (2006.01)

(52) U.S. Cl.
CPC .......... *A61K 31/4535* (2013.01); *A61K 8/4973* (2013.01); *A61K 45/06* (2013.01)

(58) Field of Classification Search
None
See application file for complete search history.

(56) References Cited

U.S. PATENT DOCUMENTS

| | | | |
|---|---|---|---|
| 5,021,426 A | 6/1991 | Baldwin et al. | |
| 5,373,005 A | 12/1994 | McCann et al. | |
| 5,853,739 A | 12/1998 | Kaslow et al. | |
| 2004/0185050 A1 | 9/2004 | Mota et al. | |
| 2006/0269605 A1 | 11/2006 | Lizio et al. | |

FOREIGN PATENT DOCUMENTS

| | | |
|---|---|---|
| EP | 1 336 608 A1 | 8/2003 |
| WO | WO 95/35287 A1 | 12/1995 |
| WO | WO 00/59884 A1 | 10/2000 |
| WO | WO 02/11757 A2 | 2/2002 |
| WO | WO 2006/051477 A2 | 5/2006 |
| WO | WO 2008/064011 A1 | 5/2008 |
| WO | WO 2009/026858 A1 | 3/2009 |

OTHER PUBLICATIONS

Drugs.com, "Ketotifen (Systemic)", Aug. 2, 2000, pp. 1-11 of 11, downloaded from "http://www.drugs.com/mmx/novo-ketotifen.html?printable=1" on Jul. 23, 2014.*
Dutta et al., Chemotherapy, 1989, vol. 35, pp. 200-207.*
International Search Report prepared by the U.S. Patent and Trademark Office on Oct. 6, 2010, for International Application No. PCT/US2010/047019.
Written Opinion prepared by the U.S. Patent and Trademark Office on Oct. 6, 2010, for International Application No. PCT/US2010/047019.
Plouffe D, et al. *In silico activity profiling reveals the mechanism of action of antimalarials discovered in a high-throughput screen.* Proc Natl Acad Sci U S A 2008;105:9059-64.
Mu J, et al. *Multiple transporters associated with malaria parasite responses to chloroquine and quinine.* Mol Microbiol 2003;49:977-989.
Liu S, Mu J, Jiang H, Su X.-z. *Effects of Plasmodium falciparum mixed infections on in vitro antimalarial drug tests and genotyping.* Am J Trop Med Hyg 2008;79:178-84.
Agrawal, Rashmi, et al., "Haem polymerase as a novel target of antimalarial action of cyproheptadine", Biochemical Pharmacology, vol. 64, No. 9, Nov. 1, 2002 pp. 1399-1406, XP002692010, ISSN: 0006-2952.
Alin, Hassan M., et al., "Multiple dose 1-14 pharmacokinetics of oral artemisinin and comparison of its efficacy with that of oral artesunate in falciparum malaria patients", Transactions of the Royal Society of Tropical Medicine and Hygiene, Elsevier, GB, vol. 90, No. 1, Jan. 1, 1996 pp. 61-65, XP004542680, ISSN: 0035-9203. DOI: 10.1016jS0035-9203(96)90480-0.
Anderson, M.O., et al., "Parallel synthesis of 9-aminoacridines and their evaluation against chloroquine-resistant Plasmodium falciparum", Bioorganic & Medicinal Chemistry, Pergamon, GB, vol. 14, No. 2, Jan. 15, 2006, pp. 334-343, XP827992281, ISSN: 0968-0896.
Brand, Verena, et al., "Influence of Amitriptyline on Eryptosis, Parasitemia and Survival of Plasmodium Berghei-Infected Mice", Cellular Physiology and Biochemistry, Karger, Basel, CH, vol. 22, No. 5-6, Jan. 1, 2008, pp. 405-412, XP009126175, ISSN: 1015-8987.

(Continued)

*Primary Examiner* — Savitha Rao
*Assistant Examiner* — Gregg Polansky
(74) *Attorney, Agent, or Firm* — Sheridan Ross P.C.

(57) ABSTRACT

The invention provides methods and compounds for the treatment and prevention of malaria infection and transmission in a mammal by administering compounds of the invention to a mammal having or suspected of having a malaria infection. The invention also provides pharmaceutical compositions that can kill or arrest the growth of *Plasmodium* organisms, and especially *Plasmodium falciparum*, thereby preventing or blocking transmission of malaria as well as treating malaria infection.

7 Claims, 1 Drawing Sheet

(56) References Cited

OTHER PUBLICATIONS

Huang, W-Z, et al., "Study on Treatment of 1-14 Plasmodium-Cynomolgi Infections of Macaque With Ketotifen", Yao Hsueh Hsueh Pao—Acta Pharmaceutica Sinica. Yaoxue Xuebao, CN, vol. 22, No. 6, Jan. 1, 1987, pp. 409-412, XP009167009, ISSN: 0513-4870.

Looareesuwan, S., et al., "Randomised trial 1-14 of artesunate and mefloquine alone and in sequence for acute uncomplicated falciparum malaria.". LANCET Apr. 4, 1992. vol. 339, No. 8797, pp. 821-824, XP002692009, ISSN: 0140-6736.

Singh, N., et al., "Causal Prophylactic 1-14 Activity of Antihistaminic Agents Against Plasmodium Yoelii Nigeriensis Infection in Swiss Mice", Acta Tropica, Elsevier Science BV, Amsterdam, NL, vol. 69, No. 3, Jun. 1, 1998, pp. 255-260, XP001086554, ISSN: 0001-706X, DOI: 10.1016/S0001-706X(97)00138-1.

Sowunmi, A., "A randomized comparison of chloroquine and chloroquine plus ketotifen in the treatment of acute, uncomplicated, Plasmodium falciparum malaria in children.", Annals of Tropical Medicine and Parasitology, vol. 97, No. 2, Mar. 2003, pp. 103-117, XP009167005.

Supplementary European Search Report, dated Apr. 16, 2013, for European Patent Application No. 10812670.7.

* cited by examiner

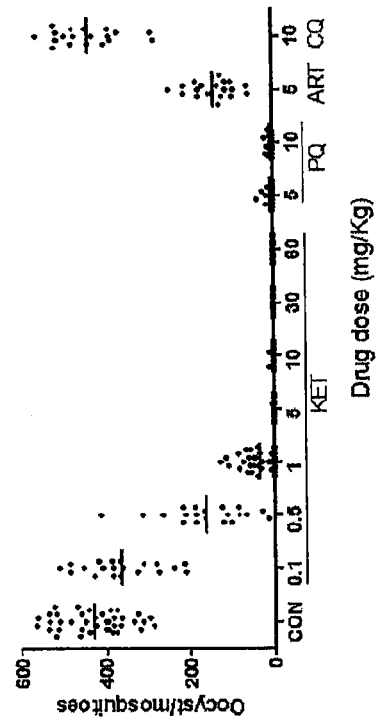
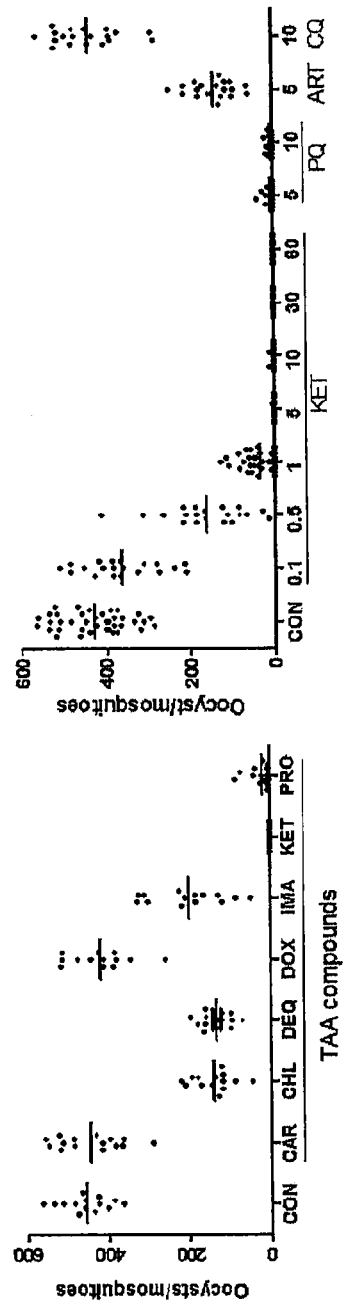
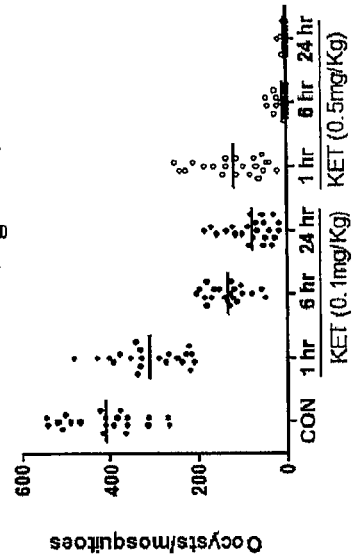
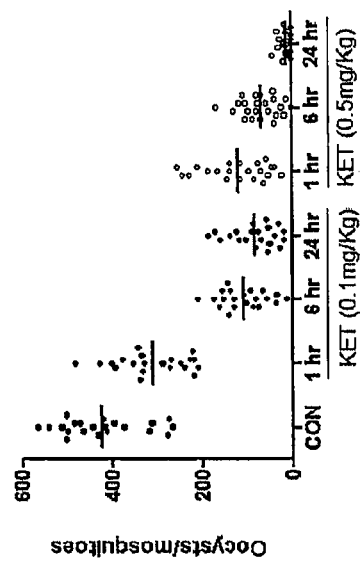
Figure 1A
Figure 1B
Figure 1C
Figure 1D

COMPOUNDS THAT TREAT MALARIA AND PREVENT MALARIA TRANSMISSION

CROSS REFERENCE TO RELATED APPLICATIONS

This application is a national stage application under 35 U.S.C. 371 of PCT Application No. PCT/US2010/047019 having an international filing date of 27 Aug. 2010, which designated the United States, which PCT application claimed the benefit of U.S. Provisional Application No. 61/237,417 filed 27 Aug. 2009, the entire disclosure of each of which is incorporated herein by reference.

GOVERNMENT INTEREST

The work performed during the development of this disclosure utilized intramural support from the National Institutes of Health. The government has certain rights in this invention.

TECHNICAL FIELD

The invention relates to therapeutic compounds, pharmaceutical compositions containing the same and their use in the prevention and treatment of malaria infection.

BACKGROUND OF INVENTION

The life cycle of *Plasmodium falciparum* is one of the most complex life cycles of any organism. The complete life cycle involves both intracellular and extracellular stages in humans, as well as in the mosquito.

Infection of a new human host is initiated when a carrier mosquito takes a blood meal. During the process of probing for food, saliva containing Sporoziotes in the mosquito's saliva is injected into the human host. While some of these sporoziotes enter the bloodstream, recent work has shown that a majority of them are deposited into the dermis and not directly into the blood. Within three hours following injection into the skin, most of the sporozoites leave the injection site via the bloodstream, the lymphatic system or direct migration through tissue. Regardless of the route taken, the sporozoite must migrate through cell barriers in both the skin and in the ultimate target organ, the liver. To this end, it has recently been shown that *Plasmodium* sporozoites are capable of traversing cells without initiating replication within the cell.

Once the sporozoites are in the bloodstream, they rapidly localize to the liver. This preference for liver tissue is mediated by an interaction between the major surface protein of sporozoites, the circumsporozoite protein (CSP), and highly sulfated proteoglycans present in loose, basement membrane of the liver. Once they have reached the liver, it appears that sporozoites actively invade Kupffer cells using a process involving gliding motility. This process, which does not involve flagella, involves interactions between parasite membrane proteins and an extracellular, polysaccharide substrates secreted by the parasite. Additionally, cell invasion involves the ordered release of proteins and other molecules from secretory organelles, called micronemes and rhoptries, present at the apical end of the zoite. The sporozoite then traverse the invaded cell, crossing into the space of Disse, and further migrating through several other hepatocytes. The sporozoite then invades a final hepatocyte, with the parasite forming an encapsulating structure referred to as a parasitophorous vacuole (PV). At this point, the organism begins liver stage (LS) growth.

Little is known about growth of the organism during the liver stage. What is known, however, is that following formation of the PV, the sporozoite differentiates into a liver trophozoite. Following this differentiation, growth and asexual replication through a process known as exoerythrocytic schizogony is rapid, requiring the ability to obtain nutrients from the host, as well as the ability to cause an increase in cell volume without damaging the host cell. This latter ability is related to the parasite's ability to confer resistance to apoptosis of the host cell. This stage of the life cycle culminates in the production of mreozoites, which are released into the blood.

Once in the blood, the parasites begin the blood stage, or erythrocytic stage of the life cycle. It is this stage of the infection that results in the pathology associated with malaria. This stage is also referred to as the ring stage, due to the ring-like morphology of the early trophozoite. During this phase, the merozoites invade erythrocytes and undergo a trophic period in which the parasite enlarges. Enlargement of the trophozoite results in active metabolism, which includes ingestion of host cytoplasm and proteolysis of hemoglobin. The trophic phase ends with multiple rounds of nuclear division resulting in the formation of schizonts. These schizonts then bud off merozoites, which are released upon rupture of the infected erythrocyte. Once released, the merozoites infect new erythrocytes, and begin another round of blood-stage replication.

During subsequent rounds of replication, some parasites switch from an asexual replication strategy to a sexual replication strategy. In this reproduction strategy, some parasites differentiate into either macrogametocytes or microgametocytes. These gametocytes, which contain a single nucleus, are large parasites that fill the entire erythrocyte. Following their release into the blood, the gametocytes are ingested by mosquitoes during the taking of a blood meal. This begins what is referred to as the sporogonic cycle.

Once in the mosquitoe's stomach, the microgametes penetrate the macrogametes, resulting tin the formation of zygotes. Soon after zygote formation, meiosis occurs and the spherical zygote transforms into an elongated motile cell called an ookinete. The ookinete uses its motile ability to penetrate the matrix surrounding the blood meal, and traverse several layers of epithelial cells before exiting through the basal side of the epithelium. Upon reaching the basal surface, the ookinete begins its transformation into an oocyst.

Maturation of the oocyst is a long process, taking approximately 12 days. During this process, the oocyst grows in size, eventually becoming 50-60 μm in diameter. At some point during this phase, sporozoites are produced. These sporozoites are mobile, although this motility is still immature. Eventually, the sporozoites are released from the oocyst, due in large part to the action of a cysteine protease called the egress cysteine protease (ECP1).

Once released, the sporozoites are carried to all tissues of the mosquito by the circulating hemolymph. Upon reaching the basal lamina of the salivary glands, ligands on the outer surface of the sporozoite interact with receptors, allowing the sporozoite to adhere to the basal surface. The parasites move through the basal lamina and invade the salivary gland acinar cells. This invasion is mediated by a short-lived vacuole that transports the sporozoite through the cytoplasm of the acinar cells, and out through the apical surface. The process ends with the sporozoite ending up in the salivary gland duct. Thus, the sporozoites are ready to infect a new host during the next blood meal.

According to the Centers for Disease Control, malaria is one of the most severe public health problems worldwide, it is the leading cause of death and disease in many developing countries, affecting mostly young children and pregnant women. Malaria is the cause of at least one million deaths every year, with 350 and 500 million clinical episodes occurring every year. More than 80% of the malaria deaths worldwide occur in Africa south of the Sahara. Currently there is no vaccine available, and there is growing resistance to existing anti-malarial drugs. Only one drug (primaquine) is used to kill non-erythrocytic stages (the gametocyte and liver stages), it has serious side effects and the concern of resistance to the only drug that can kill non-erythrocytic stages prevents wide use of this drug. Thus, there is an urgent need for new malarial drugs and particularly drugs that can effectively treat non-erythrocytic stages thereby disrupting the infectious cycle of the infective organisms to prevent transmission between individuals during the non-infectious gametocyte and liver stages and to eradicate the infection in an individual before the erythrocytic stage develops.

SUMMARY OF INVENTION

The present invention is drawn to compounds that can kill malaria gametocytes to block malaria transmission and treat malaria infection in the non-erythrocytic stages, as well as therapeutic uses of these molecules to prevent or slow the transmission of *Plasmodium* organisms between mammals and eliminate or prevent infection in a mammal.

The present inventors have identified compounds effective for the treatment and prevention of malaria transmission by integrating quantitative high-throughput screening (qHTS) with genetic mapping.

Screens of seven malaria parasite lines revealed a large number of consensus actives (active in both replicates or active in one replicate and inconclusive in the other), all of which inhibited parasite growth. 1,279 compounds were tested and about 20% to 30% were active in most lines except W2, where 40% were active, and D10 and Dd2, where 19% and 15% were active, respectively. Of the hundreds of inhibitors identified for each line, about 50% or more showed $IC_{50}$ values between 1 and 10 µM and 6% to 14% had $IC_{50}$ values less than 1 µM. There were 155 compounds that inhibited growth in all seven lines tested and 25 compounds were identified that inhibited proliferation in all parasite lines at lower than 2 µM $IC_{50}$. Some of those 25 compounds are well known antimalarial drugs (such as quinacrine), while others have not previously been used for malaria prophylaxis or treatment.

Thus, the present invention provides compounds that can kill or arrest the growth of *Plasmodium* organisms, and especially *Plasmodium falciparum*, thereby preventing or blocking transmission of malaria as well as treating malaria infection, including in the non-erythrocytic stages. The present invention also provides pharmaceutical compositions containing these compounds. The invention also provides methods of using these compounds and pharmaceutical compositions to treat malaria infection in a subject and to prevent or slow the development of malaria infection, including the non-erythrocytic stages of the disease.

Thus, one embodiment of the invention is a method of treating a malaria infection in a mammal by administering to a mammal in need of such treatment, a therapeutically effective amount of at least one compound of the invention.

One embodiment of the invention is a method of preventing a malaria infection by administering to a mammal in need of such treatment, a therapeutically effective amount of a compound of the invention that blocks malaria transmission by killing *Plasmodium* organisms in the non-erythrocytic stages of the parasite's life cycle. In a preferred embodiment, the administered compound kills the *Plasmodium* gametocytes.

Another embodiment of the invention is a method of treating or eliminating a malaria infection in a mammal by administering to a mammal harboring a *Plasmodium* organism in a non-erythrocytic stage or suspected of having been infected with a *Plasmodium* organism, a therapeutically effective amount of a compound of the invention that blocks malaria transmission by killing *Plasmodium* organisms in the non-erythrocytic stages of the parasite's life cycle and/or blocking oocyst formation in the mosquito midgut. In a preferred embodiment, the administered compound kills the *Plasmodium* gametocytes. In these embodiments, the compound of the invention may be administered in conjunction (either simultaneously or sequentially) with an "artemisinin compound" such as artemisinin, artesunate, artemether and dihydroartemisinin. Preferably, in these embodiments, the compound of the invention is administered in conjunction (either simultaneously or sequentially) with a "third therapeutically-effective anti-malaria compound" such as at least one of lumefantrine, amodiaquine, mefloquine, sulfadoxine, and pyrimethamine. More preferably, in these embodiments, the compound of the invention is administered with both an artemisinin compound and a third therapeutically-effective anti-malaria compound to effectively treat erythrocytic stages as well as non-erythrocytic stages of malaria. Thus, with the three-drug combination, the artemisinin compound and/or the third therapeutically-effective anti-malaria compound effectively treat symptoms of malaria while a compound of the invention, preferably ketotifen, blocks transmission of the infecting *Plasmodium* organism.

In one aspect, the compounds of the invention that are useful in the methods of the present invention include at least one of an antihistamine, a tricyclic antidepressant, A serotonin receptor antagonist, a dihydrofolate reductase (DHFR) inhibitor, a Na+ channel blocker, a mast cell stabilizing agent, an endothelial nitric oxide synthase inhibitor, a selective blocker of apamin-sensitive K+ channels, a folic acid antagonist, a muscarinic receptor antagonist, an inducer of apoptosis, a K+ channel blocker, a known antimalarial, a monoamine oxidase inhibitor, an anti-amoebic, an inhibitor of amyloid "42 fibril formation, an inhibitor of microtubule assembly, a selective acetylcholinesterase inhibitor, a modulator of M2 muscarinic acetylcholine receptor activity, a selective PDGF tyrosine kinase receptor inhibitor, a CYP1A1 and DNA topoisomerase II inhibitor, an inhibitor of free radical lipid peroxidation, a DNA synthesis inhibitor, a calcineurin phosphatase inhibitor, an antineoplastic, a DNA topoisomerase I inhibitor, a protonophoric anthelmintic, an adrenoceptor antagonist, a Ca2+ ionophore, a potassium-sparing diuretic, an antibiotic, an acetylcholinesterase inhibitor, a vasoconstrictor, and, an adrenoceptor blocker.

In a specific embodiment, the compounds of the invention that are useful in the methods of the present invention include at least one of an antihistamine, a tricyclic antidepressant, a serotonin receptor antagonist, a dihydrofolate reductase (DHFR) inhibitor, and a Na+ channel blocker.

In another aspect, the compounds of the invention that are useful in the methods of the present invention include at least one of ketotifen, dequalinum dichloride, doxipin, protyptiline, carbita pentane, MLS000708402-02, NCGC00163169-03, MLS000556883-02, MLS000556884-02, cryphoheptidine, cryphoheptidine, desloratadine, sumotil, desloratadine, quetiapine, quetiapine, amitriptyline, butriptyline, desipramine, doxepin, nortriptyline, rimipramine, amitriptylinoxide, butriptyline, clomipramine, dosulepin, dothiepin, doxepin, imipramine, imipraminoxide, lofepramine, trimipramine, desipramine, norpramin, pertofrane, nortriptyline, protriptyline, demexiptiline, dibenzepin, dimetacrine, iprindole melitracen, metapramine, nitroxazepine, noxiptiline, propizepine, quinupramine, amineptine, opipramol, tianeptine, cianopramine, cyanodothiepin, flutracen, amoxapine, maprotiline, mianserin, mirtazapine, setiptiline, oxaprotiline, diphenhydramine, doxylamine, loratadine, desloratadine, fexofenadine, pheniramine, cetirizine, promethazine, chlorpheniramine, levocetirizine, quetiapine, meclizine, dimenhydrinate, cimetidine, famotidine, ranitidine, nizatidine, roxatidine, lafutidine, protriptyline, trimipramine, cyproheptadine, trifluoperazine, topotecan, doxorubicin, mitoxantrone, iclaprim, amiloride, benzamil, quinidine sulfate, quinine sulfate, quinacrine dihydrochloride, diphenyleneiodonium chloride, dequalinium dichloride, para-fluoro-hexahydrosila-difenidol (p-FHHSiD), emetine dihydrochloride hydrate, pentamidine isethionate, dequalinium analog, paclitaxel, tyrphostin A9, ellipticine, mitoxantrone, cyclosporin A, idarubicin, (S)-(+)-camptothecin, niclosamide, propafenone hydrochloride, calcimycin, (S)-(-)-propafenone hydrochloride, 2'-(4-Aminophenyl)-[2,5'-bi-1H-benzimidazol]-5-amine (Ro 90-7501), 1,5-bis(4-allyldimethylammoniumphenyl)pentan-3-one dibromide (BW284c51), WB 64, U-83836 dihydrochloride, aminopterin, methotrexate, halofantrine, pyrimethamine, triamterene, trimethoprim, 1,5-Bis(4-allyldimethylammoniumphenyl)pentan-3-one dibromide, mefloquine, artemisinin, and, dihydroergotamine methanesulfonate.

In a preferred aspect of the invention, the compounds of the invention that are useful in the methods of the present invention include a compound of Formula I:

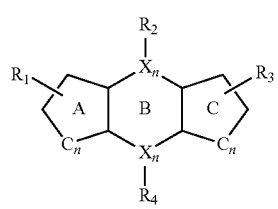

Formula I wherein;

X is C, N or S; and n=1 or 2 (i.e. the A and C rings may be 5-7 membered rings, the B ring may be a 6-8 membered ring, preferably the A and C rings are 6-membered rings and the B ring is a 7-membered ring, each of the A, B, and C rings may be cycloalkyl or aryl, preferably, the A and C rings are aryl and the B ring is cycloalkyl)

$R_1$, $R_2$, and $R_3$ are each, independently, H, carbonyl, $NR_5R_6$, halide, $C_{1-6}$ alkyl, $C_{3-8}$ cycloalkyl, $C_{2-4}$ alkenyl, $C_{2-4}$ alkynyl, or $C_{1-4}$ alkoxy, aryl, or $C_{1-6}$ alkyl optionally substituted with $NR_5R_6$, hydroxy, mercapto, halide, $C_{1-6}$ alkyl, $C_{1-6}$ alkenyl, $C_{1-4}$ alkoxy, aryl, heteroaryl, or a combination thereof;

$R_4$ is H, $NR_5R_5$, halide, $C_{1-6}$ alkyl, $C_{3-8}$ cycloalkyl, $C_{2-4}$ alkenyl, $C_{2-4}$ alkynyl, $C_{1-4}$ alkoxy, aryl, 4-cyclohexylidene-1-methylpiperidine, methylpropan-1-amine, N,N-dimethylpropan-1-amine, N,N, 2-trimethylpropan-1-amine, 1-propyl-4-methylpiperazine, or $C_{1-6}$ alkyl optionally substituted with hydroxy, mercapto, halide, $C_{1-6}$ alkyl, $C_{1-6}$ alkenyl, $C_{1-4}$ alkoxy, cyclo alkyl, heterocyclic, aryl, heteroaryl, or a combination thereof;

$R_5$ and $R_6$ are each, independently, H, $C_{1-6}$ alkyl, $C_{3-8}$ cycloalkyl, $C_{2-4}$ alkenyl, $C_{2-4}$ alkynyl, or $C_{1-4}$ alkoxy.

In another embodiment, the invention is a method of preventing a malaria infection in a mammal by administering to the mammal at least one of the compounds of the invention.

In these methods, the compounds of the invention may be administered as their pharmaceutically acceptable salts, pharmaceutically acceptable solvates, tautomers, racemates, polymorphs, pure enantiomers, diastereoisomers, metabolites, prodrugs or N-oxides.

Additionally, one aspect of the invention is a pharmaceutical composition containing one or more of the compounds of the invention with at least one pharmaceutically acceptable carrier. A related aspect of the invention is a pharmaceutical composition comprising at least one prodrug of the therapeutic compounds of the invention, with at least one pharmaceutically acceptable carrier. A related aspect of the invention is a pharmaceutical package comprising a pharmaceutical composition comprising therapeutically-effective amounts of at least one compound of the invention, optionally together with at least one pharmaceutically acceptable carrier. The pharmaceutical compositions may be administered separately, simultaneously or sequentially, with other compounds or therapies used in the prevention, treatment, prevention of transmission, or amelioration of symptoms of, malaria.

Also provided herein are pharmaceutical kits containing a pharmaceutical composition of at least one prodrug of the invention, optionally together with at least one pharmaceutically acceptable carrier; prescribing information and a container. The prescribing information may describe the administration, and/or use of these pharmaceutical compositions alone or in combination with other therapies used in the prevention, treatment or amelioration of malaria.

Also provided herein are methods for the prevention, treatment, prevention of transmission, or prophylaxis of malaria in a mammal comprising administering to a mammal in need thereof therapeutically effective amounts of any of the pharmaceutical compositions of the invention, including, for example, the pharmaceutical compositions comprising at least one prodrug of the compounds of the invention.

Other aspects of the invention will be set forth in the accompanying description of embodiments, which follows and will be apparent from the description or may be learned by the practice of the invention. However, it should be understood that the following description of embodiments is given by way of illustration only since various changes and modifications within the spirit and scope of the invention will become apparent to those skilled in the art and are encompassed within the scope of this invention.

BRIEF DESCRIPTION OF DRAWINGS

FIG. 1, shows in vivo gametocytocidal activities of TAA compounds. Mice infected with *Plasmodium yoelii nigeriensis* were treated with drugs in different concentrations for various time periods and were exposed to mosquitoes. Oocysts were counted from dissected midgut 9-10 days after feeding. FIG. 1A, the number of oocysts from mosquitoes fed on mice treated with different TAA compounds for 1 hour. CAR, carbita Pentane (100 mg/kg); CHL, chlorpromazine (30 mg/kg); DEQ, dequalinium dichloride (10 mg/kg); Dox, doxipin hydrochloride (30 mg/kg); Ima, Imipramine (100 mg/kg), KET, ketotifen (100 mg/kg); Pro, protryptiline hydrochloride (10 mg/kg). FIG. 1B, the number of oocysts from mosquitoes fed on mice treated with different concentrations of ketotifen (KET) for 1 hour, compared with those treated with standard anti-malarial drugs, primaquine (PQ, 5 and 10 mg/kg), arteminisinin (ART, 5 mg/kg) and chloroquine (CQ, 10 mg/kg). FIG. 1C, the number of oocysts from mosquitoes fed on mice treated with a single dose of 0.5 mg/kg or 0.1 mg/kg of ketotifen (KET) for 1, 6 or 24 hours. FIG. 1D, the number of oocysts from mosquitoes fed on mice treated with two doses of 0.5 mg/kg or 0.1 mg/kg (filled symbol) of ketotifen (KET) for 1, 6 or 24 hours. CON, no drug control.

DESCRIPTION OF EMBODIMENTS

The present inventors have identified targets of chemical compounds in malaria parasites by integrating quantitative high-throughput screening (qHTS) with genetic mapping. Seven *P. falciparum* lines were tested, including parents of three genetic crosses, for their responses to 1,279 bioactive compounds from the LOPAC collection of known bioactives (Sigma-Aldrich). Using progeny from a genetic cross and genetic transfection methods of allelic replacement, candidate genes were identified for three differential chemical phenotypes (DCPs) that show distinct signature responses to compounds among a variety of parasite isolates. These results showed that differential responses of small molecules between parasite lines is a reliable phenotype for exploring molecular mechanisms of pharmacologic interest in malaria treatment and prevention.

Thus, the present invention is drawn to methods of preventing or treating malaria infection, and particularly to killing *Plasmodium* organisms infecting a mammal in the erythrocyte and non-erythrocyte stages by administering at least one of the compounds of the invention. The invention encompasses methods of preventing or limiting the transmission of *Plasmodium* organisms from one mammal to another, by the administration of at least one of the compounds of the invention to one or more of the mammals.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication commensurate with a reasonable benefit/risk ratio.

"Pharmaceutically-acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines, or alkali or organic salts of acidic residues such as carboxylic acids. Pharmaceutically-acceptable salts include the conventional non-toxic salts or the quaternary ammonium salts of the parent compound formed, for example, from non-toxic inorganic or organic acids. Such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like. Pharmaceutically acceptable salts are those forms of compounds, suitable for use in contact with the tissues of human beings and animals without excessive toxicity, irritation, allergic response, or other problem or complication, commensurate with a reasonable benefit/risk ratio.

Pharmaceutically-acceptable salt forms of compounds provided herein are synthesized from the parent compound which contains a basic or acidic moiety by conventional chemical methods. Generally, such salts are, for example, prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in at page 1418 of Remington's Pharmaceutical Sciences, 17th ed., Mack Publishing Company, Easton, Pa., 1985.

"Prodrugs" are intended to include any covalently bonded carriers that release an active parent drug of the present invention in vivo when such prodrug is administered to a mammalian subject. Since prodrugs are known to enhance numerous desirable qualities of pharmaceuticals (i.e., solubility, bioavailability, half life, manufacturing, etc.) the compounds of the present invention may be delivered in prodrug form. Thus, the present invention is intended to cover prodrugs of the presently claimed compounds, methods of delivering the same, and compositions containing the same. Prodrugs of the present invention are prepared by modifying functional groups present in the compound in such a way that the modifications are cleaved, either in routine manipulation or in vivo, to a compound of the invention. Prodrugs include compounds of the present invention wherein an acyl, hydroxy, amino, or sulfhydryl group is bonded to any group that, when the prodrug of the present invention is administered to a mammalian subject, is cleaved to form a free acetyl, hydroxyl, free amino, or free sulfydryl group, respectively. Examples of prodrugs include, but are not limited to, acetate, formate, and benzoate derivatives of alcohol and amine functional groups in the compounds of the present invention.

The term "therapeutically effective amount" of a compound of this invention means an amount effective to modulate the formation or progression of a malaria infection in a host.

It will be appreciated by those skilled in the art that compounds of the invention having a chiral center may exist in, and may be isolated in, optically active and racemic forms. It is to be understood that the compounds of the present invention encompasses any racemic, optically-active, regioisomeric or stereoisomeric form, or mixtures thereof, which possess the therapeutically useful properties described herein. It is well known in the art how to prepare optically active forms (for example, by resolution of the racemic form by recrystallization techniques, by synthesis from optically-active starting materials, by chiral synthesis, or by chromatographic separation using a chiral stationary phase). It is also to be understood that the scope of this invention encompasses not only the various isomers, which may exist but also the various mixtures of isomers, which may be formed. For example, if the compound of the present invention contains one or more chiral centers, the compound can be synthesized enantioselectively or a mixture of enantiomers and/or diastereomers can be prepared and separated. The resolution of the compounds of the present invention, their starting materials and/or the intermediates may be carried out by known procedures, e.g., as described in the four volume compendium Optical Resolution Procedures for Chemical Compounds: Optical Resolution Information Center, Manhattan College, Riverdale, N.Y., and in Enantiomers, Racemates and Resolutions, Jean Jacques, Andre Collet and Samuel H. Wilen; John Wiley & Sons, Inc., New York, 1981, which is incorporated in its entirety by this reference. Basically, the resolution of the compounds is based on the differences in the physical properties of diastereomers by attachment, either chemically or enzymatically, of an enantiomerically pure moiety resulting in forms that are separable by fractional crystallization, distillation or chromatography.

The compounds used in making the pharmaceutical compositions of the present invention may be purchased commercially. Additionally, some of the compounds of the invention may be purchased commercially. The compounds of the present invention, including the salts and prodrugs of these compounds, may also be prepared in ways well known to one skilled in the art of organic synthesis. These compounds of this invention may be prepared using the reactions performed in solvents appropriate to the reagents and materials employed and suitable for the transformation being effected. It is understood by one skilled in the art of organic synthesis that the functionality present on various portions of the molecule must be compatible with the reagents and reactions proposed. Such restrictions to the substituents, which are compatible with the reaction conditions, will be readily apparent to one skilled in the art and alternate methods must then be used.

Also provided herein are pharmaceutical compositions containing compounds of the invention and a pharmaceutically-acceptable carrier, which are media generally accepted in the art for the delivery of biologically active agents to animals, in particular, mammals. Pharmaceutically-acceptable carriers are formulated according to a number of factors well within the purview of those of ordinary skill in the art to determine and accommodate. These include, without limitation: the type and nature of the active agent being formulated; the subject to which the agent-containing composition is to be administered; the intended route of administration of the composition; and, the therapeutic indication being targeted. Pharmaceutically-acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, well known to those of ordinary skill in the art. Descriptions of suitable pharmaceutically-acceptable carriers, and factors involved in their selection, are found in a variety of readily available sources, such as Remington's Pharmaceutical Sciences, 17th ed., Mack Publishing Company, Easton, Pa., 1985.

This invention further provides a method of treating a mammal afflicted with a malaria infection or preventing a mammal from developing malaria, which includes administering to the mammal a pharmaceutical composition provided herein. Such compositions generally comprise a therapeutically effective amount of a compound provided herein, that is, an amount effective to prevent, ameliorate, lessen or inhibit a malaria infection in a mammal. Such amounts typically comprise from about 0.1 to about 1000 mg of the compound per kilogram of body weight of the mammal to which the composition is administered. Therapeutically effective amounts can be administered according to any dosing regimen satisfactory to those of ordinary skill in the art.

Administration may be, for example, by various parenteral means. Pharmaceutical compositions suitable for parenteral administration include various aqueous media such as aqueous dextrose and saline solutions; glycol solutions are also useful carriers, and preferably contain a water soluble salt of the active ingredient, suitable stabilizing agents, and if necessary, buffering agents. Antioxidizing agents, such as sodium bisulfite, sodium sulfite, or ascorbic acid, either alone or in combination, are suitable stabilizing agents; also used are citric acid and its salts, and EDTA. In addition, parenteral solutions can contain preservatives such as benzalkonium chloride, methyl- or propyl-paraben, and chlorobutanol.

Alternatively, compositions can be administered orally in solid dosage forms, such as capsules, tablets and powders; or in liquid forms such as elixirs, syrups, and/or suspensions. Gelatin capsules can be used to contain the active ingredient and a suitable carrier such as, but not limited to, lactose, starch, magnesium stearate, stearic acid, or cellulose derivatives. Similar diluents can be used to make compressed tablets. Both tablets and capsules can be manufactured as sustained release products to provide for continuous release of medication over a period of time. Compressed tablets can be sugar-coated or film-coated to mask any unpleasant taste, or used to protect the active ingredients from the atmosphere, or to allow selective disintegration of the tablet in the gastrointestinal tract.

A preferred formulation of the invention is a mono-phasic pharmaceutical composition suitable for parenteral or oral administration for the prevention, treatment or prophylaxis of a malaria infection, consisting essentially of a therapeutically-effective amount of at least one compound of the invention, and a pharmaceutically acceptable carrier. In a preferred embodiment, the invention is a mono-phasic pharmaceutical composition suitable for parenteral or oral administration for the prevention, treatment or prophylaxis of a malaria infection, consisting essentially of a therapeutically-effective amount of ketotifen, and a pharmaceutically acceptable carrier. In another preferred embodiment, the invention is a mono-phasic pharmaceutical composition suitable for parenteral or oral administration for the prevention, treatment or prophylaxis of a malaria infection, consisting essentially of a therapeutically-effective amount of ketotifen and an artemisinin compound, and a pharmaceutically acceptable carrier. In another preferred embodiment, the invention is a mono-phasic pharmaceutical composition suitable for parenteral or oral administration for the prevention, treatment or prophylaxis of a malaria infection, consisting essentially of a therapeutically-effective amount of ketotifen, an artemisinin compound, and a third therapeutically-effective anti-malaria compound, in a pharmaceutically acceptable carrier. In these embodiments, the "artemisinin compounds" are selected from artemisinin, artesunate, artemether and dihydroartemisinin. In these embodiments, the "third therapeutically-effective anti-malaria compound" is preferably at least one of lumefantrine, amodiaquine, mefloquine, sulfadoxine, and pyrimethamine. In these embodiments, the artemisinin compound and/or the third therapeutically-effective anti-malaria compound effectively treat erythrocytic stages and a compound of the invention, preferably ketotifen, effectively treat non-erythrocytic stages of malaria. Thus, with the three-drug combination, the artemisinin compound and/or the third therapeutically-effective anti-malaria compound effectively treat symptoms of malaria while a compound of the invention, preferably ketotifen, blocks transmission of the infecting *Plasmodium* organism.

Another preferred formulation of the invention is a mono-phasic pharmaceutical composition suitable for parenteral or oral administration for the prevention, treatment or prophylaxis of a malaria infection in a mammal consisting essentially of a therapeutically-effective amount of a prodrug of at least one of the compounds of the invention, and a pharmaceutically acceptable carrier.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as wetting agents, emulsifying agents and dispersing agents. It may also be desirable to include isotonic agents, such as sugars, sodium chloride, and the like in the compositions. In addition, prolonged absorption of the injectable pharmaceutical form may be brought about by the inclusion of agents which delay absorption such as aluminum monosterate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which in turn may depend upon crystal size and crystalline form. Alternatively, delayed absorption of a parenterally-administered drug is accomplished by dissolving or suspending the drug in an oil vehicle.

Injectable depot forms are made by forming microencapsule matrices of the drug in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue. The injectable materials can be sterilized for example, by filtration through a bacterial-retaining filter.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation is then subdivided into unit dosage forms of the type described above containing from, for example, 0.1 to about 500 mg of the therapeutic compounds of the present invention.

Formulations of the invention suitable for oral administration may be in the form of capsules, cachets, pills, tablets, powders, granules or as a solution or a suspension in an aqueous or non-aqueous liquid, or an oil-in-water or water-in-oil liquid emulsions, or as an elixir or syrup, or as pastilles (using an inert base, such as gelatin and glycerin, or sucrose and acacia), and the like, each containing a predetermined amount of a compound or compounds of the present invention as an active ingredient. A compound or compounds of the present invention may also be administered as bolus, electuary or paste.

In solid dosage forms of the invention for oral administration (capsules, tablets, pills, dragees, powders, granules and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monosterate; (8) absorbents, such as kaolin and bentonite clay; (9) lubricants, such as talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may be employed as fillers in soft and hard-filled gelatin capsules using such excipients as lactose or milk sugars, as well as high molecular weight polyethylene glycols and the like.

A tablet may be made by compression or molding optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter. These compositions may also optionally contain opacifying agents and may be of a composition that they release the active ingredient only, or preferentially, in a certain portion of the gastrointestinal tract, optionally, in a delayed manner. Examples of embedding compositions which can be used include polymeric substances and waxes. The active ingredient can also be in microencapsulated form.

The tablets or pills of the present invention may be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

Liquid dosage forms for oral administration of the compounds of the invention include pharmaceutically-acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or salicylate, and which is solid at room temperature, but liquid at body temperature and, therefore, will melt in the rectum or vaginal cavity and release the active compound. Formulations of the present invention which are suitable for vaginal administration also include pessaries, tampons, creams, gels, pastes, foams or spray formulations containing such carriers as are known in the art to be appropriate.

Dosage forms for the topical or transdermal administration of compounds of this invention include powders, sprays, ointments, pastes, creams, lotions, gels, solutions, patches, drops and inhalants. The active ingredient may be mixed under sterile conditions with a pharmaceutically-acceptable carrier, and with any buffers, or propellants which may be required.

The ointments, pastes, creams and gels may contain, in addition to an active ingredient, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an active ingredient, excipients such as lactose, talc, silicic acid, aluminum hydroxide, calcium silicates and polyamide powder or mixtures of these substances. Sprays can additionally contain customary propellants such as chlorofluorohydrocarbons and volatile unsubstituted hydrocarbons, such as butane and propane.

Transdermal patches have the added advantage of providing controlled delivery of compounds of the invention to the body. Such dosage forms can be made by dissolving, dispersing or otherwise incorporating one or more compounds of the invention in a proper medium, such as an elastomeric matrix material. Absorption enhancers can also be used to increase the flux of the compound across the skin. The rate of such flux can be controlled by either providing a rate-controlling membrane or dispersing the compound in a polymer matrix or gel.

Pharmaceutical formulations include those suitable for administration by inhalation or insufflation or for nasal or intraocular administration. For administration to the upper (nasal) or lower respiratory tract by inhalation, the compounds of the invention are conveniently delivered from an insufflator, nebulizer or a pressurized pack or other convenient means of delivering an aerosol spray. Pressurized packs may comprise a suitable propellant such as dichlorodifluoromethane, trichlorofluoromethane, dichlorotetrafluoroethane, carbon dioxide, or other suitable gas. In the case of a pressurized aerosol, the dosage unit may be determined by providing a valve to deliver a metered amount.

Alternatively, for administration by inhalation or insufflation, the composition may take the form of a dry powder, for example, a powder mix of one or more compounds of the invention and a suitable powder base, such as lactose or starch. The powder composition may be presented in unit dosage form in, for example, capsules or cartridges, or, e.g., gelatin or blister packs from which the powder may be administered with the aid of an inhalator, insufflator or a metered-dose inhaler.

For intranasal administration, compounds of the invention may be administered by means of nose drops or a liquid spray, such as by means of a plastic bottle atomizer or metered-dose inhaler. Typical of atomizers are the Mistometer (Wintrop) and Medihaler (Riker).

Drops, such as eye drops or nose drops, may be formulated with an aqueous or nonaqueous base also comprising one or more dispersing agents, solubilizing agents or suspending agents. Liquid sprays are conveniently delivered from pressurized packs. Drops can be delivered by means of a simple eye dropper-capped bottle or by means of a plastic bottle adapted to deliver liquid contents dropwise by means of a specially shaped closure.

The formulations may be presented in unit-dose or multi-dose sealed containers, for example, ampules and vials, and may be stored in a lyophilized condition requiring only the addition of the sterile liquid carrier, for example water for injection, immediately prior to use. Extemporaneous injection solutions and suspensions may be prepared from sterile powders, granules and tablets of the type described above.

The dosage formulations provided by this invention may contain the therapeutic compounds of the invention, either alone or in combination with other therapeutically active ingredients, and pharmaceutically acceptable inert excipients. The term 'pharmaceutically acceptable inert excipients' includes at least one of diluents, binders, lubricants/glidants, coloring agents and release modifying polymers.

Suitable antioxidants may be selected from amongst one or more pharmaceutically acceptable antioxidants known in the art. Examples of pharmaceutically acceptable antioxidants include butylated hydroxyanisole (BHA), sodium ascorbate, butylated hydroxytoluene (BHT), sodium sulfite, citric acid, malic acid and ascorbic acid. The antioxidants may be present in the dosage formulations of the present invention at a concentration between about 0.001% to about 5%, by weight, of the dosage formulation.

Suitable chelating agents may be selected from amongst one or more chelating agents known in the art. Examples of suitable chelating agents include disodium edetate (EDTA), edetic acid, citric acid and combinations thereof. The chelating agents may be present in a concentration between about 0.001% and about 5%, by weight, of the dosage formulation.

The dosage form may include one or more diluents such as lactose, sugar, cornstarch, modified cornstarch, mannitol, sorbitol, and/or cellulose derivatives such as wood cellulose and microcrystalline cellulose, typically in an amount within the range of from about 20% to about 80%, by weight.

The dosage form may include one or more binders in an amount of up to about 60%) w/w. Examples of suitable binders include methyl cellulose, hydroxypropyl cellulose, hydroxypropylmethyl cellulose, polyvinyl pyrrolidone, eudragits, ethyl cellulose, gelatin, gum arabic, polyvinyl alcohol, pullulan, carbomer, pregelatinized starch, agar, tragacanth, sodium alginate, microcrystalline cellulose and the like.

Examples of suitable disintegrants include sodium starch glycolate, croscarmellose sodium, crospovidone, low substituted hydroxypropyl cellulose, and the like. The concentration may vary from 0.1% to 15%, by weight, of the dosage form.

Examples of lubricants/glidants include colloidal silicon dioxide, stearic acid, magnesium stearate, calcium stearate, talc, hydrogenated castor oil, sucrose esters of fatty acid, microcrystalline wax, yellow beeswax, white beeswax, and the like. The concentration may vary from 0.1% to 15%, by weight, of the dosage form.

Release modifying polymers may be used to form extended release formulations containing the therapeutic compounds of the invention. The release modifying polymers may be either water-soluble polymers, or water insoluble polymers. Examples of water-soluble polymers include polyvinylpyrrolidone, hydroxy propylcellulose, hydroxypropyl methylcellulose, vinyl acetate copolymers, polyethylene oxide, polysaccharides (such as alginate, xanthan gum, etc.), methylcellulose and mixtures thereof. Examples of water-insoluble polymers include acrylates such as methacrylates, acrylic acid copolymers; cellulose derivatives such as ethylcellulose or cellulose acetate; polyethylene, and high molecular weight polyvinyl alcohols.

Another embodiment of the invention relates to the use of any of the prodrug compounds or compositions described herein in the preparation of a medicament for the treatment or prevention of malaria or transmission of malaria.

Another embodiment of the invention relates to the use of any of the compounds or compositions described herein in the preparation of a medicament for the prevention or treatment of malaria in a mammal. The prevention may include the prevention of transmission of malaria between mammals.

Each publication or patent cited herein is incorporated herein by reference in its entirety.

Additional objects, advantages, and novel features of this invention will become apparent to those skilled in the art upon examination of the following examples thereof, which are not intended to be limiting.

EXAMPLES

Example 1

Screening of Bioactive Compounds Using a *Plasmodium* Proliferation Assay

*P. falciparum* proliferation was tested within infected erythrocytes against the LOPAC-1280 collection of known bioactives (Sigma-Aldrich: sigmaaldrich.com/chemistry/drug-discovery/validation-libraries/lopacl280-navigator.html) by a qHTS 10 of a SYBR DNA binding assay (Plouffe D, et al. *In silico activity profiling reveals the mechanism of action of antimalarials discovered in a high-throughput screen*. Proc Natl Acad Sci USA 2008;105:9059-64.). The *P. falciparum* lines used in this study have been described previously (Mu J, et al. *Multiple transporters associated with malaria parasite responses to chloroquine and quinine*. Mol Microbiol 2003;49:977-989). The SYBR Green viability assay was adapted from methods described previously (Plouffe D, et al. *In silico activity profiling reveals the mechanism of action of antimalarials discovered in a high-throughput screen*. Proc Natl Acad Sci USA 2008;105:9059-64; Kato N, et al. *Gene expression signatures and small-molecule compounds link a protein kinase to Plasmodium falciparum motility*. Nat Chem Biol 2008;4:347-56). Briefly, 3 µl culture medium was dispensed into 1536-well black clear-bottom plates (Aurora Biotechnologies) using a Multidrop Combi (Thermo Fisher Scientific Inc.); 23-nL compounds in DMSO were added by a pin tool (Kalypsys), and 5 µl of *P. falciparum*-infected RBCs (0.3% parasitemia, 2.5% hematocrit final concentration) were added. The plates were incubated at 37° C. in a humidified incubator in 5% CO2 for 72 h, and 2 µl lysis buffer (20 mM Tris-HCl, 10 mM EDTA, 0.16% saponin, 1.6% triton-X, 10× SYBR Green I supplied as 10,000× final concentration by Invitrogen) was added to each well. The plates were mixed for 25 sec with gentle shaking and incubated overnight at room temperature in the dark. The following morning, fluorescence intensity at 485 (14) nm excitation and 535 (25) nm emission wavelengths was measured on an EnVision (Perkin Elmer) plate reader. The LOPAC1280 collection was screened against each line at eight (seven for Dd2) five-fold dilutions beginning at 29 µM. Antimalarial drugs, 2 and 3, and DMSO were included as positive and negative controls for each plate, respectively. Follow-up SYBR Green assays in 96-well plate format were performed as described (Liu S, Mu J, Jiang H, Su X. -z. *Effects of Plasmodium falciparum mixed infections on in vitro antimalarial drug tests and genotyping*. Am J Trop Med Hyg 2008;79:178-84). Briefly, 150 µl synchronized parasites diluted to 1% parasitemia with 1% hematocrit were mixed with 50 µl medium containing compound. Compound stocks (10 mM) were dissolved in ethanol or DMSO and tested at 11 two-fold dilutions in triplicate. The beginning concentration of each compound was adjusted depending on $IC_{50}$ values from the initial qHTS. The plates were incubated at 37° C. under 5% CO2, 5% O2, and 90% N2 for 72 h, incubated for another 30 min after addition of 50 µl lysis buffer, and read in a FLUOstar OPTIMA reader (BMG Labtech). Data were analyzed using software at the NIAID Bioinformatic Resources (niaid-biocluster.niaid.nih.gov/cgi-bin/bipod2/index.cgi). Parasite proliferation was measured after 72 hr of incubation (corresponding to 1.5 generations of intra-erythrocytic parasite growth), with each compound tested at seven or eight five-fold dilutions beginning at 29 µM. Two independent screens of each parasite line performed well, showing 0.7 or higher average Z' factor and eight-fold or higher signal-to background ratio. The potencies of known antimalarial agents had similar values determined by the assay in 96-well plate format. Titrations of two control inhibitors were present on every plate and showed expected $IC_{50}$ values. The antimalarial agents chloroquine and quinine were present in the collection, and $IC_{50}$ values determined from the qHTS for 5 were similar, but the measurements for 4 were 15- to 20-fold higher than those from 96-well plate tests because of lower solubility of 4 in dimethyl sulfoxide (DMSO). Although the determined potencies of 4 were lower, the relative potency between lines sensitive to 4, HB3, 3D7, and D10 were clearly distinguished from resistant lines. The consensus $IC_{50}$ and activity values for each of the 1,279 compounds were established and screening data are deposited in PubChem (AID 1828). Comparison of the replicate runs for each parasite line indicated excellent agreement of curve class assignment and $IC_{50}$ determination. About 80% of actives identified in one replicate were active in the second replicate for all lines except Dd2,where 55% were active in both replicates. Of the actives that did not repeat, almost all showed inconclusive activity in the other replicate with few or none scoring as inactive. The potencies of compounds scored as active or inconclusive in both replicates correlated well indicating good repeatability in determining $IC_{50}$ values between replicates.

Example 2

Discovery of Potential Antimalarial Compounds

Screens of the seven parasite lines revealed a large number of consensus actives (active in both replicates or active in one replicate and inconclusive in the other), all of which inhibited parasite growth. Among the 1,279 compounds tested, about 20% to 30% were active in most lines except W2, where 40% were active, and D10 and Dd2, where 19% and 15% were active, respectively. Of the hundreds of inhibitors identified for each line, about 50% or more showed $IC_{50}$ values between 1 and 10 μM and 6% to 14% had $IC_{50}$ values less than 1 μM. There were 155 compounds that inhibited growth in all seven lines tested. The potency distribution of these pan inhibitors indicated differences in sensitivity between the lines; W2 was most sensitive, with 32% of the compounds having $IC_{50}$ values of 1 μM or less, while Dd2 was least sensitive with 7% below 1 μM. We identified 25 potent compounds that inhibited proliferation in all parasite lines at lower than 2 μM IC50. Some of these compounds are well known antimalarial drugs, while others such as hexahydro-sila-difenidol hydrochloride, dequalinium dichloride, taxol, and BW 284c51 are not compounds used for malaria prophylaxis or treatment.

Example 3

Discovery of *Plasmodium* Gametocytocidal Compounds 2,816 FDA approved drugs were screened against two *Plasmodium falciparum* parasites, one producing functional gametocytes and the other producing no gametocytes, and identified approximately 41 compounds that showed differences between the two parasites (5 folds differences in $IC_{50}$) in response to the drugs.

For testing transmission-blocking activity in vivo, CD-1 strain female mice, aged 6-8 weeks old, were infected intraperitoneally (i.p.) with 5×106 P. *yoelii nigeriensis*. In a preliminary experiment, on day 3 post infection the animals were administrated i.p. a single dose of tricyclic antihistamine and antidepressants (TAA) compound or pharmaceutical-grade phosphate buffer saline (pH 7.4). Starting 1 hr after the administration of the TAA compound, the animals were anesthetized and brought into contact with a colony of *Anopheles stephensi* mosquitoes. The mosquitoes were allowed to feed on the mice. Unfed or partially engorged mosquitoes were removed from the cages. The mosquitoes were maintained for 9-10 days 24 ±1° C. and 80-90% relative humidity. The gametocidal activity of the test compound was accessed on the basis of the oocyst counts in mosquitoes fed on treated animals and a control group. In subsequent experiments, the gametocytocidal action of ketotifin at different concentrations and doses was evaluated similarly. One group was given a single dose of 0.1, 0.5, 1, 5, 10, 30 or 60 mg/kg on day 3 post infection and subjected to mosquito feeding 1 hr after compound administration. Primaquine, chloroquine and artemisin were used as reference drugs. The other group was given one dose or two doses of 0.1 or 0.5 mg/kg at 4 hr interval and subjected to mosquito feeding 1, 6 or 24 hrs after the final drug administration.

Whereas mosquitoes fed on mice without drug treatment had an average of 460 oocysts per mosquito, mosquitoes fed on mice treated with ketotifen (100 mg/kg) and protryptiline hydrochloride (10 mg/kg) showed a strong reduction in oocyst formation (FIG. 1A). In particular, ketotifen dramatically reduced the number of oocysts to an average of 34 oocysts per mosquito at 1 mg/kg, and almost completely blocked oocyst development at 5 mg/kg after treatment for 1 hr (FIG. 1B). The oocyst counts from 5 mg/kg ketotifen treatment group (0.13 oocysts per mosquito; 2 of 44 mosquitoes had oocysts) were also significantly lower than those of 5 mg/kg primaquine treatment group (6 oocysts per mosquito; 7 of 21 mosquitoes had oocysts). Further reduction in oocyst counts was also obtained using a single dose of 0.5 and 0.1 mg/kg of ketotifen when treatment times were extended to 24 hours prior to mosquito feeding (12 and 82 oocysts per mosquito, respectively) (FIG. 1C). Two doses of 0.5 mg/kg or 0.1 mg/kg each with 4 hours interval of drug administration were also tested (FIG. 1D). Whereas the oocyst counts in double-dose treatment of 0.1 mg/kg with 24-hour treatment time (80 oocysts per mosquito) were similar to those of single-dose treatment, double-dose treatment of 0.5 mg/kg with 24-hour treatment almost completely eliminated oocysts in the mosquitoes (2 oocysts per mosquito; 4 of 23 mosquitoes had oocysts).

Compounds that showed differences in response between gametocyte producing and non-producing parasites were effective in killing gametocytes. In particular, the compound ketotifen was very effective in blocking oocyst formation in mosquito, achieving similar reduction in oocyst count to primaquine using a dose that is 10% of that of primaquine. Ketotifen can also completely kill *P. falciparum* gametocytes in vitro at 0.5 μM. Similar tricyclic structures were tested in mice and in vitro, and many were found to be active in blocking oocyst formation. These compounds are drugs that can be used to block parasite transmission.

The foregoing description of the present invention has been presented for purposes of illustration and description. Furthermore, the description is not intended to limit the invention to the form disclosed herein. Consequently, variations and modifications commensurate with the above teachings, and the skill or knowledge of the relevant art, are within the scope of the present invention. The embodiments described hereinabove are further intended to explain the best mode known for practicing the invention and to enable others skilled in the art to utilize the invention in such, or other, embodiments and with various modifications required by the particular applications or uses of the present invention. It is intended that the appended claims be construed to include alternative embodiments to the extent permitted by the prior art.

What is claimed is:

1. A method of preventing or slowing the transmission of *Plasmodium* organisms between mammals by blocking oocyst formation and transmission of a *Plasmodium* parasite comprising administering to a mammal infected with malaria parasite or suspected of being infected with malaria parasite, artemisinin and one or two doses of ketotifen administered in doses of between 0.1 mg/kg and 0.5 mg/kg of ketotifen.

2. The method of claim 1, wherein the administering further comprises administration of a therapeutically-effective amount of at least one drug selected from the group consisting of artesunate, artemether, dihydroartemisinin, lumefantrine, amodiaquine, mefloquine, sulfadoxine, and pyrimethamine.

3. The method of claim 1, wherein the ketotifen is administered as a single dose.

4. The method of claim 1, wherein the ketotifen is administered as two doses.

5. The method of claim 1, wherein the ketotifen is administered as a single dose of 0.5 mg/kg of ketotifen.

6. The method of claim 1, wherein the ketotifen is administered as two doses of 0.5 mg/kg of ketotifen.

7. The method of claim 1, wherein the artemisinin is administered at a dose of 5 mg/kg of artemisinin.

* * * * *